United States Patent [19]

Bezuglov et al.

[11] Patent Number: 4,665,214
[45] Date of Patent: May 12, 1987

[54] 15(R+S)-FLUORO-11,15-DIDEOXYPROSTA-GLANDIN $E_1$ DERIVATIVES

[75] Inventors: Vladimir v. Bezuglov, Lev D. Bergelson, Kapiton M. Lakin, Vladimir A. Makarov, Sergei G. Kovalev, all of Moscow; Yanis F. Freimanis, Riga, all of U.S.S.R.

[73] Assignee: Institut Organicheskogo Sinteza An Latr. SSR; Institut Biorgenicheskoi Khimii An SSSR; Moskovsky Meditsinsky Stomatologichesky Institut

[21] Appl. No.: 824,006
[22] PCT Filed: Apr. 24, 1985
[86] PCT No.: PCT/SU85/00029
  § 371 Date: Dec. 27, 1985
  § 102(e) Date: Dec. 27, 1985
[87] PCT Pub. No.: WO85/04875
  PCT Pub. Date: Nov. 7, 1985

[30] Foreign Application Priority Data
  Apr. 24, 1984 [SU] U.S.S.R. .................. 3731856

[51] Int. Cl.⁴ .......................................... C07C 177/00
[52] U.S. Cl. ........................... 560/121; 562/503
[58] Field of Search ................. 560/121; 562/503

[56] References Cited
FOREIGN PATENT DOCUMENTS
959785 9/1982 U.S.S.R. .................. 560/121

OTHER PUBLICATIONS
Kogtev, Bioorg Khim, 10 1260 (1984).
Guidebook on Pharmacotherapy for Doctors, part 1, 9th rev. and enl.

Primary Examiner—Robert Gerstl
Attorney, Agent, or Firm—Ladas & Parry

[57] ABSTRACT

Novel derivatives of 15(R+S)-fluoro-11,15-dideoxyprostaglandin $E_1$ of the general formula:

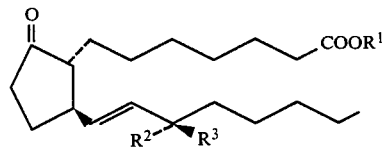

wherein R' is ethyl, methyl, hydrogen, sodium, $R^2$ or $R^3$ is hydrogen or fluorine.

The compounds according to the present invention have a high antiaggregation activity of a protracted effect.

3 Claims, No Drawings

15(R+S)-FLUORO-11,15-DIDEOXYPROSTAGLANDIN $E_1$ DERIVATIVES

FIELD OF THE INVENTION

The present invention relates to chemistry and, more particularly, to novel derivatives of 15(R+S)-fluoro-11,15-dideoxyprostaglandin $E_1$.

BACKGROUND OF THE INVENTION

Known in the art are various substances lowering aggregation of thrombocytes such as Dipirodomole (cf. M. D. Mashkovsky, Pharmaceutical Chemicals, Moscow, Medicina Publishing House, 1984, vol. 1, p. 420–421).

However, this preparation does not exhibit a high antiaggregation activity.

Known in the art are derivatives of 15-fluoroprostanic acids having a close chemical structure, e.g. 15-fluoro-15-deoxyprostaglandin $E_1$, 15-fluoro-15-deoxyprostaglandin $J_2$ which lower the aggregation power of thrombocytes. (Cf. USSR Inventor's Certificate No. 959785 Cl. C 07 C 177/00, A 61 K 31/557, 1982).

However, these compounds under the conditions of incubation with blood plasma rich in thrombocytes lose substantially their antiaggregation activity already within 30–45 minutes which hinders their use in medicobiological experiments.

Furthermore, the synthesis of these compounds is a multistaged one and proceeds with a low yield of the final product. For these reasons the above-specified compounds have not obtained a wide application in medical practice.

DISCLOSURE OF THE INVENTION

The 15(R+S)-fluoro-11,15-dideoxyprostaglandin $E_1$ derivatives are novel and hitherto unknown in the literature.

The present invention is directed to the provision of novel compounds possessing a high antiaggregation activity of a protracted duration and obtained by a simple procedure.

This object is accomplished by that the novel derivatives of 15(R+S)-fluoro-11,15-dideoxyprostaglandin $E_1$ according to the present invention have the following general formula:

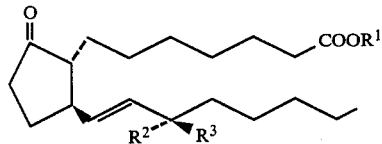

wherein: $R'$ is $CH_3$, $C_2H_5$, H, Na; $R^2$ and $R^3$ and each H or fluorine.

The compounds according to the present invention comprise colourless viscous liquids which, as a rule, are well soluble in organic solvents and only sparingly soluble in water. The exception is the sodium salt of 15(R+S)-fluoro-11,15-dideoxyprostaglandin $E_1$ ($R'$=Na) which is moderately soluble in water.

The compounds according to the present invention possess a protracted antiaggregation effect.

The antiaggregation effect of the derivatives of 15(R+S)-fluoro-11,15-dideoxyprostanglandin $E_1$ has been studied in in vitro experiments carried out by the Born Method.

To 0.9 ml of a blood plasma rich in thrombocytes 0.1 ml of a solution of a fluorinated derivative of prostanglandin is added which solution has been prepared by dissolution of an aliquote amount of a standard prostanglandin solution in dimethylsulphoxide (10 mg/ml) in 0.1 ml of a physiological solution and containing 5 μg of the compound, in the first sample—methyl ether of 15(R+S)-fluoro-11,15-dideoxyprostanglandin $E_1$, in the second sample—ethyl ether of 15(R+S)-fluoro-11,15-dideoxyprostanglandin $E_1$, in the third sample—methyl ether of 15-fluoro-15deoxyprostaglandin $E_1$, in the 4-th sample—methyl ether of 15-fluoro-15-deoxyprostanglandin $J_2$. The samples are subjected to incubation for 10 minutes at room temperature, then added with adenosindiphosphate in the final concentration of 2 μg/ml. In the control instead of the aliquote of prostanglandin the physiological solution is added which contains the same amount of dimethylsulphoxide. In the 1-st sample reduction of aggregation of thrombocytes by 80% is noticed, in the second—by 85%, in the third—by 85% and in the fourth—by 79% as compared to the control. Within 60 minutes in the 3-rd sample and within 120 minutes in the 4-th the aggregation of thrombocytes induced by adenosindiphosphates is returned to the initial level. By the same moment (60 minutes) in the 1-st and 2-nd samples there is observed the reduction of aggregation of thrombocytes by 30% and more as compared to the control. The same effect is also observed for methyl ether of 15(R+S)-fluoro-11,15-dideoxyprostanglandin $E_1$ for the period of 120 minutes.

Under similar conditions a maximum reduction of aggregation of thrombocytes caused by the known preparation dipiridomole is 48% as compared to the control. The test results are shown in Tables 1 and 2 hereinbelow.

Therefore, the 15(R+S)-fluoro-11,15-dideoxyprostanglandin $E_1$ derivatives according to the present invention exhibit a higher antiaggregation activity than the preparation dipiridomole and are superior over the known derivatives of 15-fluoroprostanic acids as regards the duration of its effect (by about 2.5 times) at an approximately equal intensity of the antiaggregation effect.

TABLE 1

| Sample No. | Test compound, 5 μg/ml | Inhibition of aggregation of thrombocytes (%) after a preliminary incubation of the test compound in plasma for 10 minutes |
|---|---|---|
| 1 | 2 | 3 |
| 1. | Methyl ether of 15(R + S)-fluoro-11,15-dideoxyprostaglandin $E_1$ ($R^1$ = $CH_3$) | 80 |
| 2. | Ethyl ether of 15(R + S)-fluoro 11,15-dideoxyprostaglandin $E_1$ ($R^1$ = $C_2H_5$) | 85 |
| 3. | Methyl ether of 15-fluoro-15-deoxyprostaglandin $E_1$ | 85 |
| 4. | Methyl ether of 15-fluoro-15-deoxyprostaglandin $J_2$ | 79 |
| 5. | 15(R + S)-fluoro-11,15-dideoxyprostaglandin $E_1$ ($R^1$ = H) | 74 |
| 6. | Sodium salt of 15(R + S)-fluoro-11,15-dideoxyprostaglandin $E_1$ ($R'$ = Na) | 67 |

TABLE 1-continued

| Sample No. | Test compound, 5 μg/ml | Inhibition of aggregation of thrombocytes (%) after a preliminary incubation of the test compound in plasma for 10 minutes |
|---|---|---|
| 1 | 2 | 3 |
| 7. | Dipiridomole | 48 |

The compounds according to the present invention are prepared from known methyl or ethyl ethers of 11-deoxyprostanglandin $E_1$ by treating a solution of the latter ethers in an organic solvent with morpholinosulphotrifluoride at a temperature below 0° C. The resulting fluorides are recovered by extraction with a suitable organic solvent, followed by purification by chromatography on silica gel. Then, if necessary, an alkaline saponification of the ethers is carried out.

TABLE 2

Duration of the antiaggregation effect of fluoroprostaglandins

| | | Change in the antiaggregation effect (as % to the initial level) after a preliminary incubation of prostaglandins in plasma for (minutes) | | | |
|---|---|---|---|---|---|
| No. | Prostaglandin, 5 μg/ml | 10 | 30 | 60 | 120 |
| 1. | Methyl ether of 15(R + S)-fluoro-11,15-dideoxyprostaglandin $E_1$ ($R^1 = CH_3$) | 100 | 75 | 50 | 50 |
| 2. | Ethyl ether of 15(R + S)-fluoro-11,15-dideoxyprostaglandin $E_1$ ($R' = C_2H_5$) | 100 | 62 | 35 | 30 |
| 3. | Methyl ether of 15-fluoro-15-deoxyprostaglandin $E_1$ | 100 | 23 | 0 | 0 |
| 4. | Methyl ether of 15-fluoro-15-deoxyprostaglandin $J_2$ | 100 | 63 | 20 | 0 |

For a better understanding of the present invention, some specific examples illustrating preparation of the compounds according to the invention are given hereinbelow.

EXAMPLE 1

100 mg (0.27 mM) of ethyl ether of 11-deoxyprostanglandin $E_1$ are dissolved in 10 ml of dry methylene chloride and the resulting solution is added, upon cooling to −78° C. and under stirring in the atmosphere of argon, to a solution of 140 μl of morpholinosulphotrifluoride in 5 ml of methylene chloride. The mixture is stirred for one hour at the temperature of −78° C., added with 2.5 ml of a saturated solution of ammonium chloride and allowed to heat to room temperature under continuous stirring. Then the reaction solution is diluted with water (7.5 ml), the aqueous layer is separated and extracted with methylene chloride. The combined organic phases are washed with a saturated solution of sodium bicarbonate (25 ml) with water to a neutral pH value, with a saturated solution of sodium chloride (15 ml) and dried with sodium sulphate. The drying agent is then filtered-off, the filtrate is evaporated, the residue is dissolved in hexane and chromatographed in a column with 10 g of silica gel (100–600 μm) is a gradient system hexane-ethylacetate to give 80.7 mg (81% of the theoretical) of ethyl ether of 15(R+S)-fluoro-11,15-dideoxyprostanglandin $E_1$ comprising a colourless viscous oil with $R_f$ 0.65 (Silufol, one spot, eluent—benzene-ethylacetate 7:1), mass spectrum (m/z): 368 (M, 2), 348 (M—HF, 7), 323 (M—$C_2H_5O$, 3), 322 (M—$C_2H_5OH$, 7), 303 (15), 302 (M—HF—$_2H_5OH$, 15), 212 (15), 192 (30), 109 (100%), $^{19}$F-NMR spectrum (δ, deuterochloroform): 170.25 (m., intensity 2.5), 171.47 (m., intensity 1); therefore, the ratio between the 15(S) and 15(R) epimers is 2.5.

EXAMPLE 2

A solution of 20 mg (0.059 mM) of 11-deoxyprostanglandin $E_1$ is 2 ml of diethyl ether upon cooling to 0° C. is treated with an excess of an ethereal solution of diazomethane. After 30 minutes the reaction mixture is evaporated to dryness, the residue is dissolved in 2 ml of methylene chloride and fluorinated in a manner similar to that described in the foregoing Example 1 using 30 μl of morpholinosulphotrifluoride. After an appropriate treatment of the reaction mixture the crude product is dissolved in hexane and chromatographed in a column with 3 g of silica gel (100–160 μm) is a gradient system hexane-ether to give 14.5 mg (70% of the theoretical) of methyl ether of 15(R+S)-fluoro-11,15-dideoxyprostanglandin $E_1$ comprising a colourless viscous oil, $R_f$ 0.37 (Silufol, one spot, hexane-ether, 2:1); mass spectrum (m/z): 354 (M, 5), 335 (M—F, 5), 334 (M—HF, 13), 323 (M—$CH_3O$, 3), 322 (M—$CH_3OH$, 7), 303 (18), 302 (M)HF—$CH_3OH$, 20), 212 (40), 192 (47), 143 (26), 109 (100%; $^1$H-NMR spectrum (δ, deuterochloroform): 5.65 (2H, m., $C_{(13)}$H, C(14)H; 4.85 (1H, d.m., $J_{HF}$ 48 Hz, $C_{15}$H); 3.61 (3H, s., $C_{(l)}OCH_3$); 2.4 (2H, m., $C_{(10)}$H); 2.25 (2H, t., $C_{(8)}$H, $C_{(12)}$H); 2.1 (2H, d.d., $C_{(2)}H_2$); 0.89 (3H, t., $C_{(19)}CH_3$); $^{19}$F NMR spectrum (δ, deuterochloroform): 170.3 (m., intensity 2.5), 171,5 (m., intensity 1); therefore, the ratio between 15(S) and 15(R) epimers is equal to 2.5.

EXAMPLE 3

A solution of 55 mg (0.16 mM) of ethyl ether of 15(R+S)-fluoro-11,15-dideoxyprostanglandin $E_1$ is 3 ml of a mixture of tetrahydrofuran-methanol (1:2) is treated with 2 ml of a 1N aqueous sodium hydroxide and the resulting mixture is allowed to stand at room temperature for 18 hours. The reaction solution is acidified with a 1N hydrochloric acid to a pH of 2–3, the organic solvents are removed by evaporation in vacuum and the residue is extracted with ethylacetate (3×15 ml). The combined organic extracts are washed with water to a neutral reaction, with a saturated solution of sodium chloride (10 ml) and dried with sodium sulphate. The drying agent is filtered-off, the filtrate is evaporated. The residue is purified by chromatography in a column with 6 g of silica gel (100–160 μm) in a gradient system chloroform-ethylacetate to give 47 mg (92% of the theoretical) of 15(R+S)-fluoro-11,15-dideoxyprostanglandin $E_1$ comprising a colourless thick oil, $R_f$ 0.75 (Silufol, one spot, benzene-dioxane-acetic acid, 40:10:1). Mass spectrum of diethyl ether produced by treatment of 1 mg of 15(R+S)-fluoro-11,15-dideoxyprostanglandin $E_1$ with an ethereal solution of diazomethane is identical to the mass spectrum given in Example 2 hereinbefore.

EXAMPLE 4

To a solution of 5 mg (0.014 mM) of 15(R+S)-fluoro-11,15-dideoxyprostanglandin $E_1$ in 5 ml of ethanol 0.375 ml of an aqueous solution of sodium carbonate (5 mg/ml) is added. The mixture is allowed to stand for one hour at room temperature and evaporated to dryness to give 5.2 mg of sodium salt of 15-(R+S)-fluoro-11,15-dideoxyprostanglandin $E_1$.

Industrial Applicability

15-Fluoro-dideoxyprostanglandins $E_1$ area chemically stable analogs of a naturally-occurring prostanglandin $E_1$, one of the most active antiaggregation factors in the organism of mammals. Furthermore, the compounds according to the present invention are stable or resistant to prostanglandindehydrogenase an enzyme initiating decomposition of prostanglandins in the organism. It has been also found that 15-fluoro-dideoxyprostanglandins $E_1$ have a moderate ability of dilating blood vessels mainly coronary ones in laboratory animals. Owing to these properties in combination with a low toxicity of over 25 mg/kg the compounds according to the present invention can be also useful as inhibitors of aggregation of thrombocytes upon conservation of blood or of thrombocytic plasma and, possibly, in operations with the use of an artificial blood circulation. The positive effect of 15-fluoro-dideoxyprostanglandins $E_1$ on vessel in conjunction with the antiaggregation effect can be useful in therapy of certain cardio-vascular diseases.

We claim:
1. A compound of the formula:

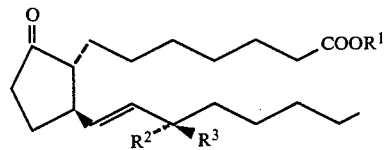

wherein R' is ethyl, methyl, hydrogen or sodium; and $R^2$ is hydrogen and $R^3$ is fluorine, or $R^2$ is fluorine and $R^3$ is hydrogen.

2. A compound according to claim 1, wherein $R^2$ is hydrogen and $R^3$ is fluorine.

3. A compound according to claim 1, wherein $R^2$ is fluorine and $R^3$ is hydrogen.

* * * * *